(12) United States Patent
Furlan et al.

(10) Patent No.: US 9,506,865 B2
(45) Date of Patent: Nov. 29, 2016

(54) ARRAY OPTICS

(71) Applicant: Roche Molecular Systems, Inc., Pleasanton, CA (US)

(72) Inventors: Alan Furlan, Zug (CH); Joachim Wietzorrek, Zug (CH)

(73) Assignee: Roche Molecular Systems, Inc., Pleasanton, CA (US)

(*) Notice: Subject to any disclaimer, the term of this patent is extended or adjusted under 35 U.S.C. 154(b) by 0 days.

(21) Appl. No.: 13/953,942

(22) Filed: Jul. 30, 2013

(65) Prior Publication Data
US 2014/0038190 A1 Feb. 6, 2014

(30) Foreign Application Priority Data

Aug. 2, 2012 (EP) .................................... 12178956

(51) Int. Cl.
| | | |
|---|---|---|
| *G01N 21/64* | (2006.01) | |
| *G02B 21/00* | (2006.01) | |
| *G02B 3/00* | (2006.01) | |
| *G02B 21/16* | (2006.01) | |

(52) U.S. Cl.
CPC ...... *G01N 21/6454* (2013.01); *G01N 21/6452* (2013.01); *G01N 21/6456* (2013.01); *G02B 3/0006* (2013.01); *G02B 3/0056* (2013.01); *G02B 21/0096* (2013.01); *G01N 2021/6478* (2013.01); *G02B 3/0068* (2013.01); *G02B 21/16* (2013.01); *G02B 2207/113* (2013.01)

(58) Field of Classification Search
None
See application file for complete search history.

(56) References Cited

U.S. PATENT DOCUMENTS

| | | | |
|---|---|---|---|
| 5,499,138 A | 3/1996 | Iba | |
| 6,686,582 B1 * | 2/2004 | Volcker | B01L 3/5085 250/216 |
| 7,218,452 B2 * | 5/2007 | Boettiger | G02B 3/0018 250/208.1 |
| 7,906,767 B2 | 3/2011 | Furlan et al. | |

FOREIGN PATENT DOCUMENTS

| | | |
|---|---|---|
| DE | 19846928 A1 | 4/2000 |
| DE | 19919092 A1 | 11/2000 |
| EP | 0395156 A1 | 4/1990 |
| EP | 2148187 A1 | 1/2010 |
| WO | 0210804 A1 | 2/2002 |

* cited by examiner

*Primary Examiner* — Neil N Turk
(74) *Attorney, Agent, or Firm* — Pamela C. Ancona; David J. Chang; M. Reza Savari (57) ABSTRACT

An instrument is disclosed with a lens system including an objective lens system. The objective lens system is disposed between a light source and the plurality of reaction regions. The objective lens system includes a field lens array, and a pupil plane, wherein the pupil plane and the light source are located on opposite sides of the field lens array. The field lens array is disposed between the light source and the plurality of reaction regions, the field lens array including a plurality of field lens array elements, wherein the radius of the curvature, the thickness and the position of the center of the curvature of any one field lens array element in the field lens array is variable and is disposed in a light beam path between the light source and the reaction regions such that any one of the field lens array elements is capable of imaging a pupil stop located between the light source and the field lens array to a pupil located on the pupil plane, wherein an array of pupils located on the pupil plane is generated by the field lens array.

8 Claims, 5 Drawing Sheets

ARRAY OPTICS

CROSS-REFERENCES TO RELATED APPLICATIONS

The present application claims the benefit of priority under 35 U.S.C. §119 of EP12178956.4, filed Aug. 2, 2012, the content of which is incorporated by reference herein in its entirety.

FIELD OF THE INVENTION

The present invention relates to the field of array optics. In particular, the present invention relates to an instrument for photometric measurement of biological liquids comprising a light source, a detector and a lens system, wherein said lens system comprises a field lens array.

BACKGROUND OF THE INVENTION

Lens systems for amplification instruments are well known in the art. One example of such a lens system is shown in U.S. Pat. No. 7,906,767. The lens system comprises a field lens, a field lens array and a pupil lens array.

The present invention provides an improved lens system for instruments for nucleic acid amplification.

SUMMARY OF THE INVENTION

In a first aspect, an instrument is disclosed including a block with a plurality of spaced apart reaction regions; a light source emitting light comprising at least one excitation frequency; a lens system comprising an objective lens system, wherein said objective lens system is disposed between the light source and the plurality of reaction regions, said objective lens system comprising a field lens array, and a pupil plane, wherein said pupil plane and said light source are located on opposite sides of the field lens array, wherein said field lens array is disposed between said light source and said plurality of reaction regions, said field lens array comprising a plurality of field lens array elements, wherein the radius of the curvature, the thickness and the position of the center of the curvature of any one field lens array element in the field lens array is variable and is disposed in a light beam path between said light source and said reaction regions such that any one of said field lens array elements is capable of imaging a pupil stop located between said light source and said field lens array to a pupil located on said pupil plane, wherein an array of pupils located on the pupil plane is generated by the field lens array; a detector disposed to receive emission light beams emitted from the plurality of reaction regions, wherein said objective lens system is further disposed between said plurality of reaction regions and said detector, and wherein said lens system additionally comprises an emission light objective between said field lens array and said detector such that the reaction regions are imaged onto the detector.

In another aspect, a method of simultaneously detecting at least one analyte contained in at least one of a plurality of reaction sites comprising the step of reacting any one of said analytes with a molecule comprising a dye is disclosed. It further comprises the step of illuminating said dye with an excitation light beam.

The excitation light beam passes a lens system disposed between a light source and the plurality of reaction regions, said lens system comprises an objective lens system, said objective lens system comprising a field lens array, and a pupil plane, wherein said pupil plane and said light source are located on opposite sides of the field lens array, wherein said field lens array is disposed between said light source and said plurality of reaction regions, said field lens array comprising a plurality of field lens array elements, wherein the radius of the curvature, the thickness and the position of the center of the curvature of any one field lens array element in the field lens array is variable and is disposed in a light beam path between said light source and said reaction regions such that any one of said field lens array elements is capable of imaging a pupil stop located between said light source and said field lens array to a pupil located on said pupil plane, wherein an array of pupils located on the pupil plane is generated by the field lens array. The method further comprises the step of detecting an emission light beam emitted by said dye using a detector, wherein said emission light beam passes said objective lens system and is focused onto said detector by an emission light objective disposed between said objective lens system and said detector.

In a further aspect, a method of illuminating a plurality of spaced-apart regions with excitation light beams is provided, comprising providing an instrument. Said instrument comprises a light source, a lens system disposed between a light source and a plurality of reaction regions, and a block including the plurality of spaced-apart reaction regions. At least one of the reaction regions comprises a sample. The lens system comprises an objective lens system which comprises a field lens array and a pupil plane. The method further comprises generating an excitation light beam with the light source, and passing the excitation light beam through the lens system, wherein any bundle of excitation light focused on the field plane of said field lens array is separated into at least two light beams. The at least two light beams are directed onto a field plane of said reaction regions by passing them through said pupil lens array, thereby irradiating said samples comprised in said reaction regions. Emission light beams are then passed from said reaction regions through said lens system.

BRIEF DESCRIPTION OF THE FIGURES

Other and further objects, features and advantages of the invention will appear more fully from the following description. The accompanying drawings, together with the general description given above and the detailed description given below, serve to explain the principles of the invention.

FIGS. 3a) and b) show perspective views of embodiments of a field lens array with variable radius, thickness and center of the curvatures.

DETAILED DESCRIPTION OF THE INVENTION

By way of illustration, specific exemplary embodiments in which the invention may be practiced now are described.

In one embodiment, an instrument is disclosed including a block with a plurality of spaced apart reaction regions; a light source emitting light comprising at least one excitation frequency; a lens system comprising an objective lens system, wherein said objective lens system is disposed between the light source and the plurality of reaction regions, said objective lens system comprising a field lens array, and a pupil plane, wherein said pupil plane and said light source are located on opposite sides of the field lens array, wherein said field lens array is disposed between said light source and said plurality of reaction regions, said field lens array comprising a plurality of field lens array elements, wherein the radius of the curvature, the thickness and the position of the center of the curvature of any one field lens array element in the field lens array is variable and is disposed in a light beam path between said light source and said reaction regions such that any one of said field lens array elements is capable of imaging a pupil stop located between said light source and said field lens array to a pupil located on said pupil plane, wherein an array of pupils located on the pupil plane is generated by the field lens array; a detector disposed to receive emission light beams emitted from the plurality of reaction regions, wherein said objective lens system is further disposed between said plurality of reaction regions and said detector, and wherein said lens system additionally comprises an emission light objective between said field lens array and said detector such that the reaction regions are imaged onto the detector.

The term "light source" as used herein can be any kind of illuminator that can be used for excitation of luminescence generated in a sample to be analyzed. The light source of the present invention can be a primary or a secondary light source, wherein a primary light source changes electrical, electromagnetic, chemical, thermal, kinetic or any other form of energy, including, e.g., light-emitting LEDs based on fluorophores, into light suitable for excitation of a marker molecule in a sample. A secondary light source is a light source which transforms the shape, direction and homogeneity of a light beam into another light beam. It can be a white source or can only contain a single wavelength, multiple wavelengths or one or more wavelength bands or combinations thereof. Typical light sources are incandescent lamps, gas discharge lamps, or light emitting diodes (LEDs) including organic LEDs (OLEDs).

The term "detector" as used herein relates to a specific arrangement of a plurality of individual detection sites that are located in the image plane of the image of the field plane. Each individual detection site is a device capable of capturing light and converting the light intensity into a corresponding electrical signal. The image of the fluorescence light originating from each sample contained in a well or vial or reaction region coincides with at least one detection site. Different fluorescence light emission pencils are all captured by different detection sites.

The terms "emission light beams" and "light emission pencils" relate to light beams originating from luminescence generated by excitation of marker molecules in the samples comprised in the wells or reaction regions. A "light emission pencil" includes all beams originating from one well or vial or reaction region comprising a sample.

An "objective lens system" comprises one or more lenses or lens arrays and optionally mirrors or other optical elements located in the beam path between the field plane and the arrangement of a plurality of individual detection sites with the purpose of generating a sharp image of the field plane across the conceptual or physical pupils onto the image plane that may or may not coincide with the surface of the arrangement of individual detection sites.

The term "field lens array" relates to a two dimensional array of field lenses all placed in or close to a field plane in an optical system. The array comprises more than one field lens array element. The "field lens array elements" are individual field lenses. A field plane is a plane that is imaged sharply onto a detector. Thus, a field plane is always located where a sharp image of an object plane is formed. An optical system may comprise one or more sharp intermediate images of an object plane and, thus, one or more field planes. The field plane is, furthermore, the location in which each light emission pencil is focused into a point. Thus, each lens positioned in a field plane has no refractive force towards these light emission pencils. A field lens does, thus, not focus a light beam, it deflects the light beam. If the field lens is not located exactly in the field plane, but is located close to the field plane, it is still a field lens if its focusing power, which depends on the focal length of the lens and its distance from the field plane, is small compared to the diameter of the beam so that the main effect of the lens is deflection, not focusing.

The term "pupil plane" as used herein relates to the plane in which one or more physical pupil stops or the image of such one or more pupil stops or pupils are located, including the pupil stop of the excitation light and the pupil stop of the emission light. A pupil stop relates to a physical aperture stop. For each pupil stop there is/are one or more pupils which are an image of a pupil stop. Each pupil stop is located near the light source or the detector. Therefore, a pupil plane coincides with the pupil stops or pupils, and the image of the pupil in the next pupil plane defines the widest diameter of a beam illuminating an object, or of the beam that images the object onto the detector.

The term "radius of the curvature" relates to the radius corresponding to the curvature of a field lens array element. Likewise, the term "position of the center of the curvature" relates to the position of the center corresponding to the curvature of a field lens array element. Thus, the radius of the curvature, the position of the center of the curvature and the thickness of each field lens array element can be adjusted such that the individual optical power and light shaping characteristics are optimized.

The calculation of the curvature of the field lens array elements and of the center of the spheres can be done by ray-tracing, a method well known to the person skilled in the art. The field lens array of the present invention is then produced by injection molding plastics or molding of glass which are also methods well known to the person skilled in the art.

As described above, the field lens array comprises a plurality of field lens array elements. The radius of the curvature, the thickness and the position of the center of the curvature of any one field lens array element in the field lens array is variable. The field lens array elements further form a monolith. Thus, the field lens array elements are no assembly of individual and independent lenses, but are made in a single block. The field lens array elements are present in the monolith with a regular spacing and a minimized space between adjacent field lens array elements. This allows separating light from different reaction regions without loss of light. The field lens array elements are not tilted against the main optical axis, i.e., tilting angles are absent. Tilting lenses would be disadvantageous as tilting makes the lenses less efficient due to stronger reflections. Tilting would, furthermore, lead to an irregular grid of the field lens array elements as the tilted lenses would have a different lateral width. The lateral width of the field lens array elements of the field lens array of the present invention, however, remains constant. By these measures, the field lens array of the present invention exhibits the properties of a field lens combined with a field lens array as described in U.S. Pat. No. 7,906,767. Thus, every field lens array element of the present invention represents, for a reaction region, a hybrid of a field lens array element according to U.S. Pat. No. 7,906,767 and a field lens. The advantage of the field lens array element of the present invention is that the optical instrument become smaller, lighter and cheaper. It is, furthermore, more efficient as two lens surfaces are omitted, each surface causing a loss of intensity. Thus, intensity is gained with the field lens array element of the present invention.

The term "emission light objective" as used herein relates to an objective which focusses light beams from the field lens array onto the detector.

The term "excitation light objective" as used herein relates to an objective lens which collimates light from a light source.

In one embodiment, the block is a heat conductive block. This makes it possible to transfer heat to the reaction vessels. In one embodiment, the block is a metal block. Metals may be selected from copper, aluminum, silver or gold. Blocks made of these metals have heat conductive properties. The block can be heated and/or cooled by different means. In one embodiment, the block is heated and cooled by Peltier elements. Thus, the temperature of the block can be varied. The block comprises a plurality of spaced-apart reaction regions. These reaction regions are accommodated by chambers comprised in said block. Reaction regions may be plastic vessels. In one embodiment, they are plastic vessels constructed and arranged to permit an optimal heat transfer between the block and a liquid comprised within said vessels. This allows for optimal conditions during thermocycling and ensures specificity and efficiency of the nucleic acid amplification. The liquid comprises reactants which can be detected by illumination with light beams. Examples of reactants are fluorescent labels which correlate with the formation of a reaction product in the liquid. One example of a reaction is an amplification reaction, such as TMA, NASBA or PCR. Such amplification reactions are well known in the art. One embodiment of reaction regions are multiwell plates.

The instrument may be a PCR instrument for real-time detection of nucleic acids during amplification.

One advantage of the different aspects of the present invention is that the lens system allows omission of costly field lenses.

One advantage of the present invention is that the objective lens system does not require two field lenses, a field lens and a field lens array, in order to obtain a high signal gain, such as the one described in U.S. Pat. No. 7,906,767. Instead, a similar signal gain can be achieved using a single field lens array as herein described. Besides cost reductions, this leads to a reduction of the complexity of the lens system and additionally, the lens system is easier to assemble and adjust.

Furthermore, the present invention allows to privilege emission light beams originating from reaction sites that are placed further from the geometrical center of the optical system, which are illuminated with lower intensity compared to the reaction sites placed closer to the geometrical center in the prior art lens systems and which, thus, emit light which is weaker. Such a privileging of the privilege emission light beams originating from reaction sites that are placed further from the geometrical center of the optical system, thus, results in a stronger and more reliable detection of the light emitted from these reaction regions.

A detector is understood to be a sensor capable of detecting light beams emitted by reactants in the reaction regions following excitation by the light emitted by the light source. Such sensors are well known to the person skilled in the art.

Lens systems of instruments according to the present invention comprise at least one lens. In one embodiment, the lens system comprises an objective lens system disposed between light source and the plurality of reaction regions. This objective lens system comprises a field lens array. The field lens array is located at or near a field plane of the lens system. The field lens array is an array comprising field lens array elements. Each of the field lens array elements has a curvature and a thickness. Each field lens array element, thus, also has a radius of the curvature and a position of the center of the curvature. The curvature can thus be defined as a segment of the circumference of a circle, and the position of the center of the curvature is then the position of the center of a hypothetical circle defined by said curvature. The term radius of the curvature is then understood by the skilled person. The radius of the curvature, the position of the center of the curvature and the thickness of said field lens array elements are variable. Thus, individual field lens array elements in the field lens array have a different radius of curvature, different centers of the curvature, and different thickness. Furthermore, the individual shaping of each field lens array element of the lens system of the present invention provides for a better homogeneity of the illumination and detection of the different reaction sites.

The lens system comprises a pupil plane located between the field lens array and the reaction regions. The field lens array is constructed and arranged to image a pupil stop located between the light source and the field lens array to a pupil on the pupil plane which is located between the field lens array and the reaction regions. In one embodiment, a regular spacing of pupil stops is present on the pupil plane. The advantage of this is that there is a better separation of the individual light beam pencils which leads to a reduction of cross talk between reaction sites. The field lens array elements, thus, act as prisms in a locally confined manner.

The term "light beam path" relates to the path taken by excitation and/or emission light beams in the lens system.

In one embodiment, the objective lens system comprises said field lens array and additionally a pupil lens array disposed between said field lens array and said plurality of reaction regions which comprises a plurality of pupil lenses, wherein said field lens array comprises a field plane, and said pupil lens array images a field point located on said field plane to a field point on a second field plane located at said reaction regions.

The term "pupil lens array" is understood to relate to an array of pupil lenses which is located at or near a pupil plane. The pupil lens array focuses the light originating from the reaction sites onto the field plane where the field lens array is placed.

The pupil lens array can focus each cluster of emission light beams onto the field plane forming a dotted image of the reaction sites. As each pencil of emission light beams is being deflected in the field plane, a much better separation between the different pencils is achieved, leading to a better illumination of the detector sites and, thus, to a better fill factor of the detector sites and, thus, a better signal. If the field lens array elements are designed such that proper pupil stops are generated between field plane and reaction regions, the pupil lens array may be omitted and the same increased fill factor may still be achieved.

In one embodiment, the pupil plane coincides with said reaction regions. The emission light is, thus, propagated to the field plane as a collimated beam. This leads to a separation of the image of the reaction sites and, thus, reduction of crosstalk. In this embodiment, the pupil lens array can be omitted, resulting in a less complex lens system with easier assembly and adjustment and reduced costs. When the pupil plane coincides with the reaction regions, the reaction regions comprise a material which is not transmissible to the excitation light beams. The material is a material which promotes mixing of the light. Crosstalk is, thus, suppressed due to the material which is not transmissible to the excitation light beams. The mixing of light improves the generation of emission light in the reaction regions. This leads to an optimization of excitation of the contents of the reaction regions.

In one embodiment, the lens system described herein additionally comprises an excitation light objective disposed between said light source and said field lens array.

Further to this, the lens system described herein may additionally comprise an excitation light filter disposed between said second objective and said field lens array. The excitation light filter allows selection of wavelengths emitted from the light source for excitation of the contents of the reaction regions. In one embodiment, an emission filter is disposed between said field lens array and said third objective. The emission filter system allows selection of specific wavelengths of the light emitted from the excited contents of the reaction regions.

The instrument described herein may additionally comprise a heating lid for providing heat to the top end of said reaction regions, said heating lid comprising openings aligned with the reaction regions, and wherein said lens system is disposed between said light source and said reaction regions such that light transmitted through said lens system is focused onto the side of the heating lid proximal to the reaction regions. The heating lid prevents evaporation of liquid in the reaction regions when the reaction regions are exposed to elevated temperature during thermal cycling.

In another aspect of the present invention, a method of simultaneously detecting at least one analyte contained in at least one of a plurality of reaction sites comprising the steps of reacting any one of said analytes with a molecule comprising a dye. It further comprises the step of illuminating said dye with an excitation light beam.

The excitation light beam passes a lens system. The lens system comprises an objective lens system disposed between a light source and the plurality of reaction regions. The objective lens system comprises a field lens array, and a pupil plane, wherein said pupil plane and said light source are located on opposite sides of the field lens array, wherein said field lens array is disposed between said light source and said plurality of reaction regions, said field lens array comprising a plurality of field lens array elements, wherein the radius of the curvature, the thickness and the position of the center of the curvature of any one field lens array element in the field lens array is variable and is disposed in a light beam path between said light source and said reaction regions such that any one of said field lens array elements is capable of imaging a pupil stop located between said light source and said field lens array to a pupil located on said pupil plane, wherein an array of pupils located on the pupil plane is generated by the field lens array. The method further comprises the step of detecting an emission light beam emitted by said dye using a detector, wherein said emission light beam passes said objective lens system and is focused onto said detector by an emission light objective disposed between said objective lens system and said detector.

Embodiments of aspects of the method and their effect are as disclosed herein.

In a further aspect of the present invention, a method of illuminating a plurality of spaced-apart regions with excitation light beams is provided, comprising providing an instrument. Said instrument comprises a light source, a lens system, and a block including the plurality of spaced-apart reaction regions. At least one of the reaction regions comprises a sample. The lens system comprises an objective lens system disposed between a light source and a plurality of reaction regions which comprises a field lens array and a pupil plane. The method further comprises generating an excitation light beam with the light source, and passing the excitation light beam through the lens system, wherein any bundle of excitation light focused on the field plane of said field lens array is separated into at least two light beams. The at least two light beams are directed onto a field plane of said reaction regions by passing them through said pupil lens array, thereby irradiating said samples comprised in said reaction regions. Emission light beams are then passed from said reaction regions through said lens system. Embodiments of features of this method and their effects are as disclosed herein.

Figure 1:
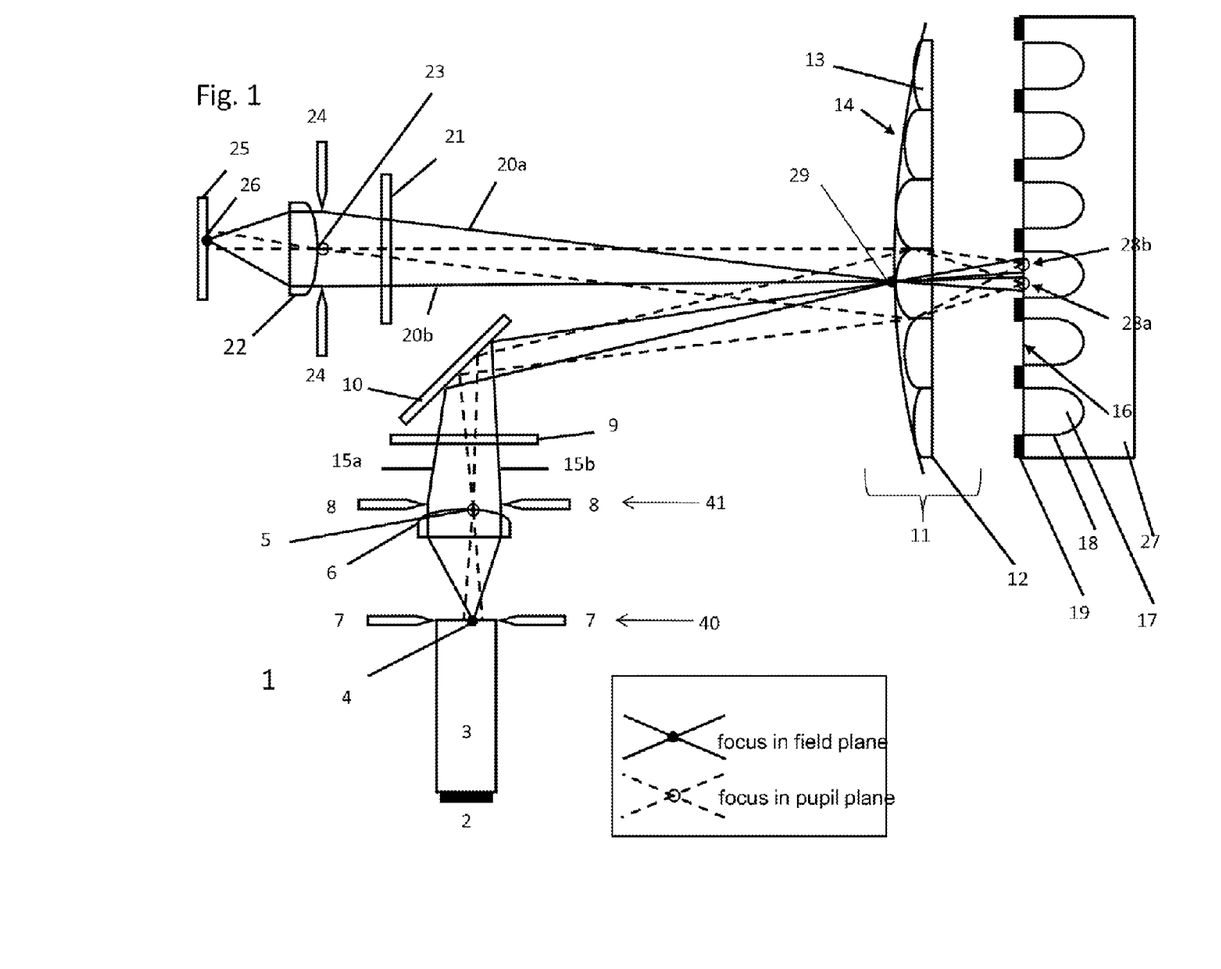
FIG. 1 shows a schematic view of an exemplary lens system with a field lens array comprising a plurality of field lens array elements, wherein the radius of the curvature, the thickness and the position of the center of the curvature of said field lens array elements in the field lens array is variable.

FIG. 1 shows an exemplary lens system (1). The lens system comprises a light source (2) and primary optics (3). An excitation field stop (7) blocks beams that are beyond its dimensions from reaching the detector (25). The lens system also comprises an excitation pupil stop (8) and an excitation objective (6). Focus point (4) is located in field plane (40) and pupil (5) is located in pupil plane (41). The lens system further comprises a filter (9) and a folding mirror (10) which directs the light beams onto the objective lens system (11). In this example, the objective lens system (11) consists of a field lens array (12). The field lens array (12) has multiple field lens array elements (13) which differ from each other. The difference is only shown schematically in this Figure and FIG. 2. The field lens array structure is shown more precisely in FIG. 3, and the field lens array from FIG. 3 thus replaces the field lens array (12) shown as a schematic example in FIGS. 1 and 2. The field lens array (12) is located near a field plane (14). Excitation light beams (15a), (15b) are shown to pass through the field lens array (12) to a pupil plane (16). In this example, the pupil plane (16) is located near the sample (17) comprised in reaction regions (18) and coincides with the heating lid (19). Reaction regions (18) are located in a block (27). Pupils (28a) and (28b) are located on the pupil plane (16). The emission light beams (20a), (20b) pass the field lens array (12), an emission filter (21) and an emission pupil stop (24). The emission objective (22) is located close to an emission pupil stop (24) in pupil plane (24) and focuses the beams (20a, 20b) onto the detector (25). The lens system (1) generates a focus point (29) of beams (15a, 15b) and (20a, 20b), and a focus point (26) of emission beams (20a, 20b).

Figure 2:
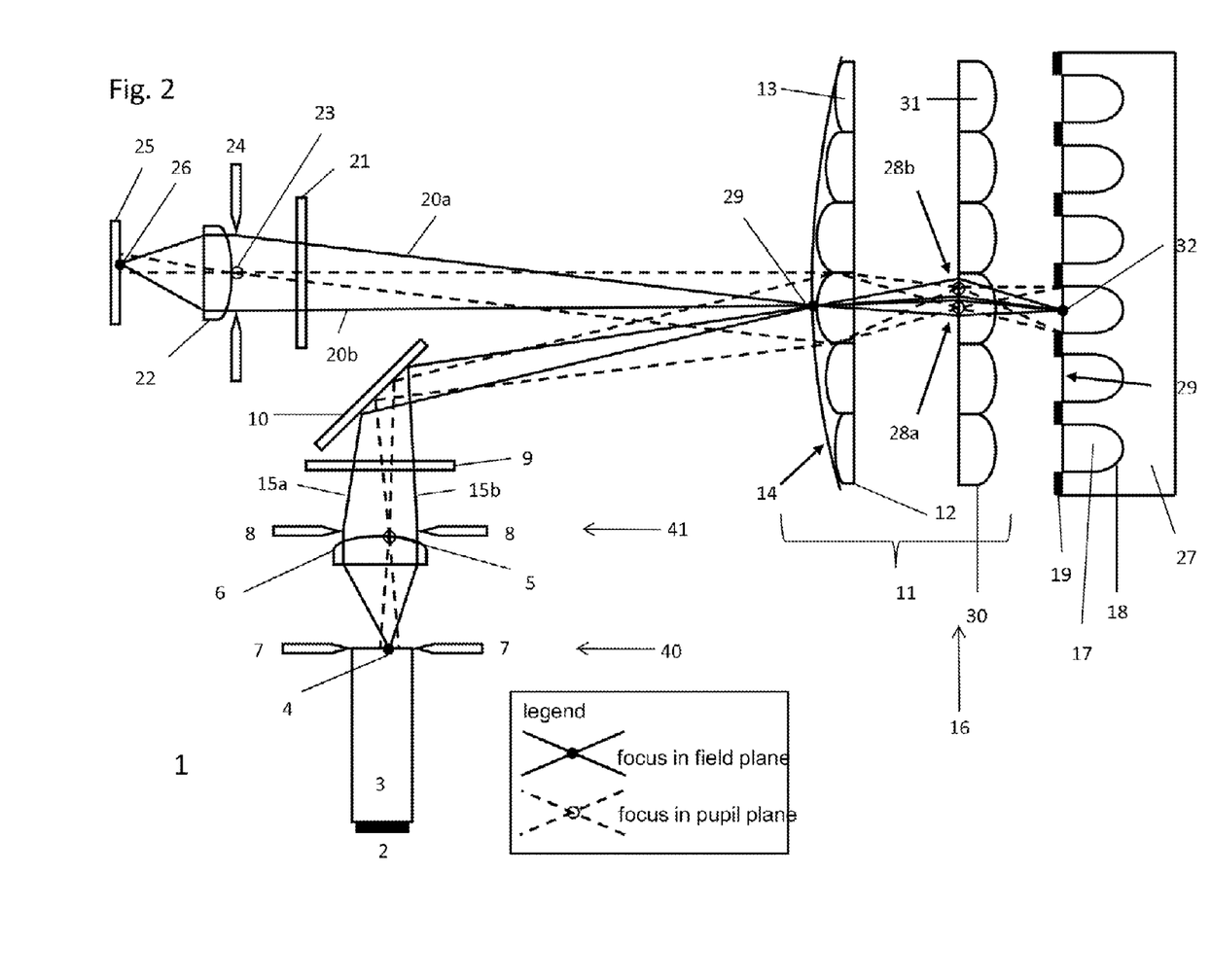
FIG. 2 shows a schematic view of a lens system with a field lens array comprising a plurality of field lens array elements, wherein the radius of the curvature, the thickness and the position of the center of the curvature of said field lens array elements in the field lens array is variable, and a pupil lens array.
Figure 3:
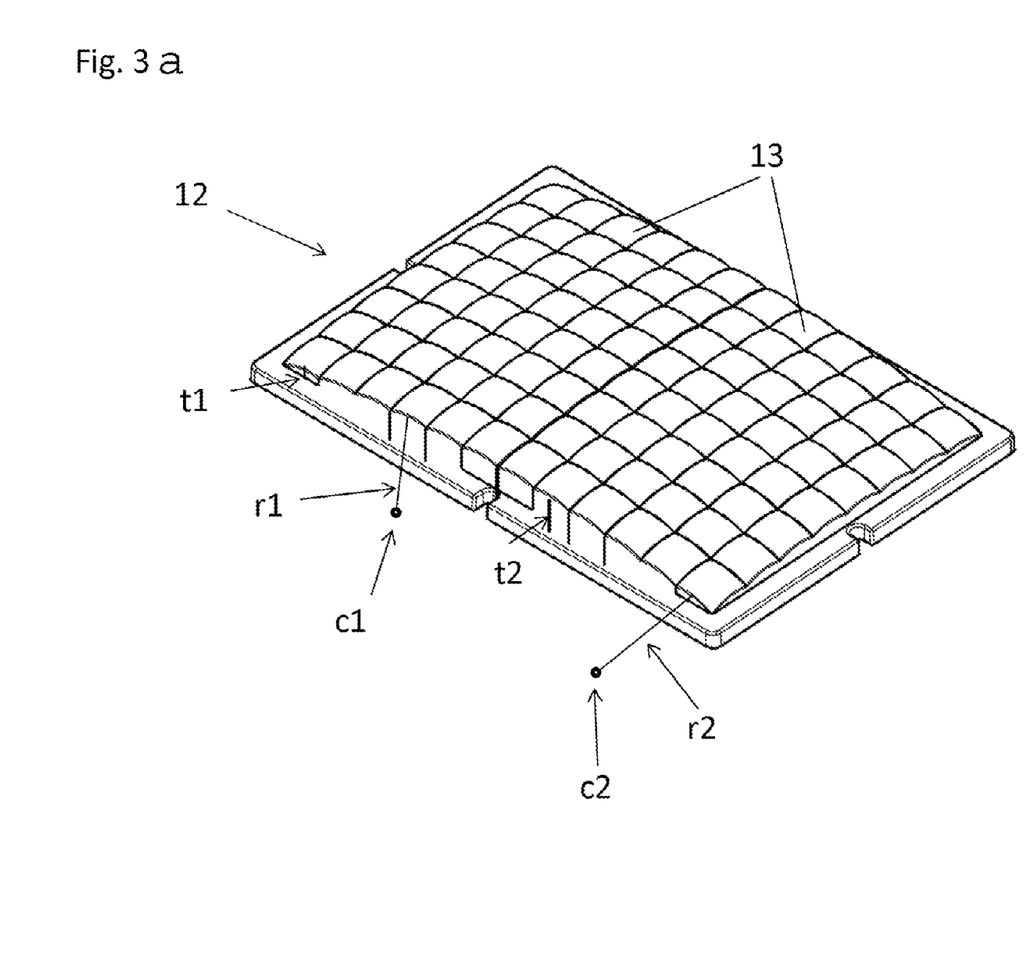

FIG. 2 shows a similar exemplary lens system (1). The difference between this lens system and the lens system of FIG. 1 is that the objective lens (11), in this example, comprises a field lens array (12) as described in FIG. 1, and, furthermore, a pupil lens array (30). The pupil lens array (30) comprises several pupil lens array elements (31) which are uniform. The pupil lens array (30) is located near a pupil plane (16) which comprises emission and excitation pupils (28a, 28b). In contrast to the lens system of FIG. 1, where the pupil plane (16) is located close to the samples, in this example, a field plane (29) is located near or coincides with the heated lid (19).

FIG. 3a) shows a field lens array (12) with field lens array elements (13) which differ in size. It can be seen from the Figure that the radius of the curvatures (e.g., r1, r2), center of the curvatures (e.g., c1, c2) and thickness (e.g., t1, t2) of the array elements (13) varies for each element (13). FIG. 3b) shows a second embodiment of a field lens array (12) with integrally formed field lens array elements (13) which have the same properties as the field lens array elements shown in FIG. 3a).

Figure 4:
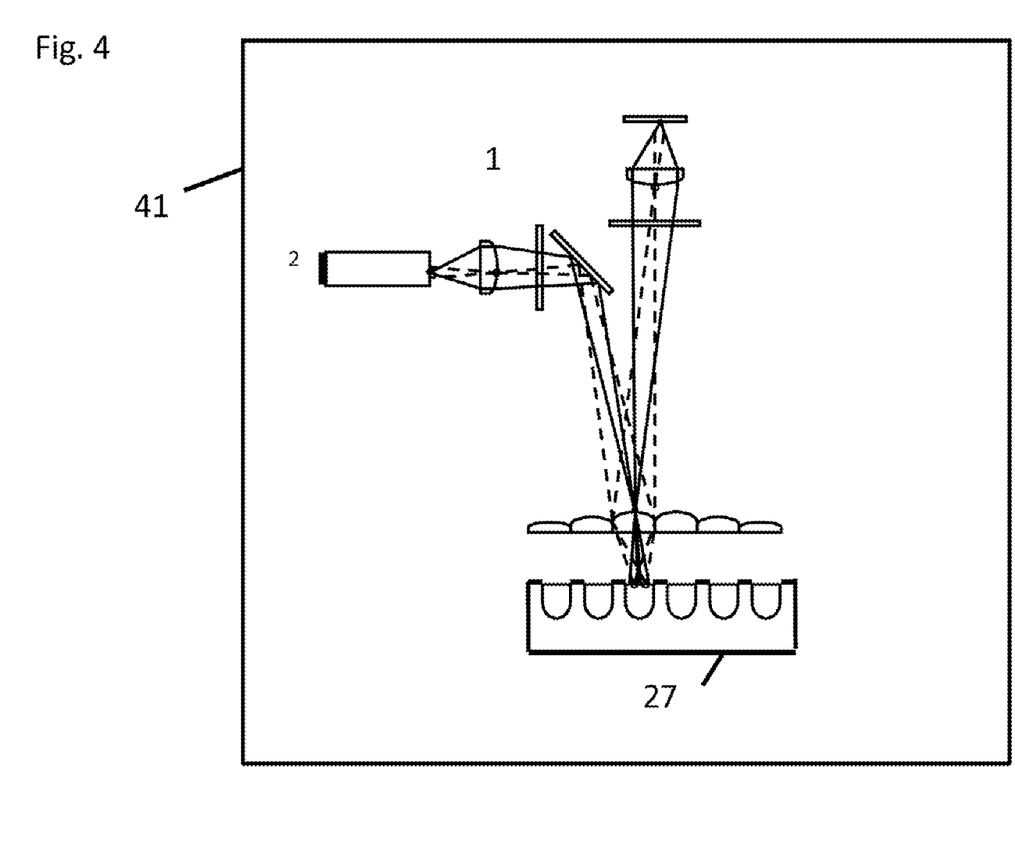
FIG. 4 shows a schematic view of an instrument with a light source and an optical system.

FIG. 4 shows an instrument (41) with a light source (2), a lens system (1) and a block (27).

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed:

1. An instrument comprising:
    a block with a plurality of spaced apart reaction regions;
    a light source emitting light comprising at least one excitation frequency;
    an objective lens system disposed between the light source and the plurality of reaction regions, said objective lens system comprising a field lens array and a pupil plane, wherein said pupil plane and said light source are located on opposite sides of the field lens array and said field lens array is disposed between said light source and said plurality of reaction regions, said field lens array comprising a plurality of field lens array elements arranged as a unitary component, each field lens array element having a radius of curvature, a thickness and a position of the center of the curvature that are different for each lens array element, each field lens array element comprises a constant lateral width, and any one of said field lens array elements is capable of imaging a pupil stop located between said light source and said field lens array to a pupil located on said pupil plane, wherein an array of pupils located on the pupil plane is generated by the field lens array, with the proviso that said instrument does not include a field lens; and
    a detector disposed to receive emission light beams emitted from the plurality of reaction regions;
    wherein said objective lens system is further disposed between said plurality of reaction regions and said detector, and wherein said instrument additionally comprises an emission light objective between said field lens array and said detector such that the reaction regions are imaged onto the detector.

2. The instrument of claim 1, wherein said light source is a light emitting diode.

3. The instrument of claim 1, wherein said objective lens system comprises said field lens array and additionally a pupil lens array disposed between said field lens array and said plurality of reaction regions which comprises a plurality of pupil lenses, wherein said field lens array comprises a field plane, and said pupil lens array images a field point located on said field plane to a field point on a second field plane located at said reaction regions.

4. The instrument of claim 1, wherein said pupil plane coincides with said reaction regions.

5. The instrument of claim 1, wherein said instrument additionally comprises an excitation light objective disposed between said light source and said field lens array.

6. The instrument of claim 1, wherein said instrument additionally comprises a heating lid for providing heat to the top end of said reaction regions, said heating lid comprising openings aligned with the reaction regions, and wherein said objective lens system is disposed between said light source and said reaction regions such that light transmitted through said objective lens system is focused onto the side of the heating lid proximal to the reaction regions.

7. A method of illuminating a plurality of spaced apart regions with excitation light beams, comprising:
    providing an instrument according to claim 1;
    generating an excitation light beam with the light source;
    passing the excitation light beam through the objective lens system, wherein any bundle of excitation light focused on the field plane of said field lens array is separated into at least two light beams;
    directing said at least two light beams onto a field plane of said reaction regions by passing them through said pupil lens array, thereby irradiating said samples comprised in said reaction regions; and
    passing emission light beams from said reaction regions through said objective lens system to said detector.

8. The instrument of claim 1, wherein said unitary component is a monolith.

* * * * *